(12) United States Patent
Sturaro et al.

(10) Patent No.: US 6,800,290 B2
(45) Date of Patent: Oct. 5, 2004

(54) VARIANTS OF ALLERGENIC PROTEINS OF THE GROUP 2 OF DERMATOPHAGOIDES

(75) Inventors: Monica Sturaro, Rome (IT); Angelo Viotti, Rome (IT); Paolo Falagiani, Milan (IT); Giovanni Mistrello, Milan (IT); Daniela Roncarolo, Milan (IT); Stefania Zanotta, Rome (IT)

(73) Assignee: Consiglio Nazionale Delle Ricerche, Rome (IT)

( * ) Notice: Subject to any disclaimer, the term of this patent is extended or adjusted under 35 U.S.C. 154(b) by 0 days.

(21) Appl. No.: 09/949,889

(22) Filed: Sep. 12, 2001

(65) Prior Publication Data

US 2002/0054881 A1 May 9, 2002

(30) Foreign Application Priority Data

Sep. 12, 2000 (IT) ..................................... MI2000A1986

(51) Int. Cl.[7] .............................................. A61K 39/35
(52) U.S. Cl. ..................... 424/275.1; 530/858; 530/868
(58) Field of Search ........................... 424/275.1, 185.1; 530/858, 868, 350

(56) References Cited

FOREIGN PATENT DOCUMENTS

JP          7-95887 A     *  5/1997

OTHER PUBLICATIONS

Mistrello et al., "Monomeric chemically modified allergens: immunologic and physicochemical characterization", ALLERGY, vol. 51, 1996, pp. 8–15.

Nishiyama et al., "Analysis of the epitope of Der f 2, a major mite allergen, by in vitro mutagenesis", Molecular Immunology, vol. 32, No. 14/15, 1995, pp. 1021–1029.

Hakkaart et al., "Epitote Mapping of the house–dust–mite allergen Der p 2 by means of site–directed mutagenesis", ALLERGY, vol. 53, 1998, pp. 165–172.

Smith and Chapman, "Localization of antigenic sites on Der p 2 using oligonucleotide–directed mutagenesis targeted to predicted surface residues", Clinical and Experimental Allergy, Blackwell Scientific Publications, vol. 27, No. 5, May 1, 1997, pp. 593–599.

Wu et al., "Major T Cell Epitote–Containing Peptides can Elicit Strong Antibody Responses" European Journal of Immunology, vol. 30, No. 1, Jan. 2000, pp. 291–299.

Mueller et al., "Hydrogen Exchange Nuclear Magnetic Resonance Spectroscopy Mapping of Antibody Epitopes on the House Dust Mite Allergen Der p 2", Journal of Biological Chemistry, vol. 276, No. 12, Mar. 2001, pp. 9359–9365.

* cited by examiner

Primary Examiner—Patrick J. Nolan
(74) Attorney, Agent, or Firm—Young & Thompson

(57) ABSTRACT

Variants of allergens of *Dermatophagoides pteronyssinus* species with reduced allergenic activity.

6 Claims, 2 Drawing Sheets

Figure 1

IgE reactivity of the modified Der p 2 allergen
(Western analysis)

Normal | Modified

μg   1 2 3   1 2 3

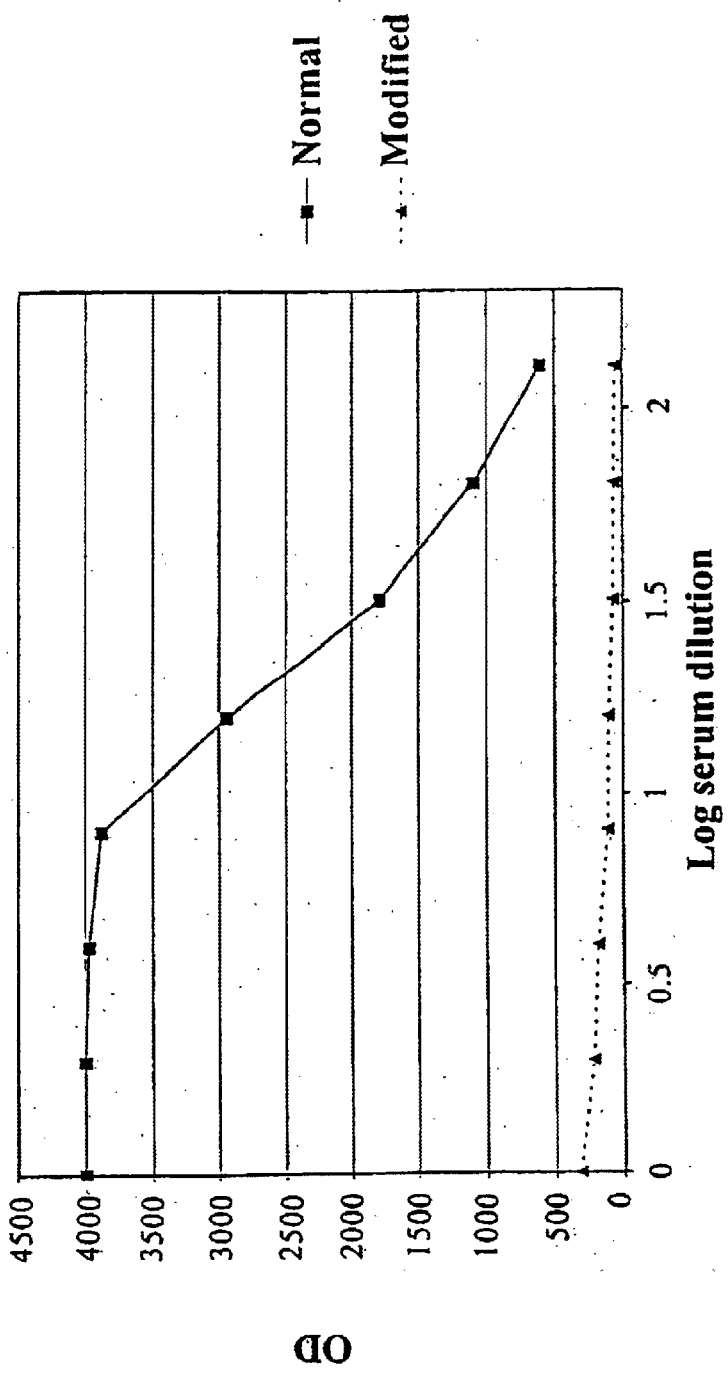

SEQUENCE LISTING

<160> NUMBER OF SEQ ID NOS: 4

<210> SEQ ID NO 1
<211> LENGTH: 444
<212> TYPE: DNA
<213> ORGANISM: Dermatophagoides pteronyssinus

<400> SEQUENCE: 1

```
aaaatgatgt acaaaatttt gtgtctttca ttgttggtcg cagccgttgc cgctgatcaa      60
gtcgatgtca aagattgtgc caatcatgaa atcaaaaaag ttttggtacc aggatgccat     120
ggttcagaac catgtatcat tcatcgtggt aaaccattcc aattggaagc cgttttcgaa     180
gccaaccaaa actcaaaaac cgctaaaatt gaaatcaaag cttcaatcga tggtttagaa     240
gttgatgttc ccggtatcga tccaaatgca tgccattata tgaaatgtcc attggttaaa     300
ggacaacaat atgatattaa atatacatgg aatgttccga aaattgcacc aaaatctgaa     360
aatgttgtcg tcactgttaa agttatgggt gatgatggtg ttttggcctg tgctattgct     420
actcatgcta aaatccgcga ttaa                                           444
```

<210> SEQ ID NO 2
<211> LENGTH: 390
<212> TYPE: DNA
<213> ORGANISM: Dermatophagoides pteronyssinus

<400> SEQUENCE: 2

```
gatcaagtcg atgtcaaaga ttgtgccaat catgaaatca aaaagtttt ggtaccagga       60 tgccatggtt cagaaccatg tatcattcat cgtggtgcac cattccaatt ggaagccgtt     120
ttcgaagcca accaaaactc agcaaccgct aaaattgaaa tcaaagcttc aatcgatggt     180
ttagaagttg atgttcccgg tatcgatcca aatgcatgcc attatatgaa atgtccattg     240
gttgcaggac aacaatatga tattaaatat acatggaatg ttccggcaat tgcaccagca     300
tctgaaaatg ttgtcgtcac tgttaaagtt atgggtgatg atggtgtttt ggcctgtgct     360
attgctactc atgctgcaat ccgcgattaa                                      390
```

<210> SEQ ID NO 3
<211> LENGTH: 145
<212> TYPE: PRT

<213> ORGANISM: Dermatophagoides pteronyssinus

<400> SEQUENCE: 3

Met Tyr Lys Ile Leu Cys Leu Ser Leu Leu Val Ala Ala Val Ala Ala
1               5                   10                  15

Asp Gln Val Asp Val Lys Asp Cys Ala Asn His Glu Ile Lys Lys Val
            20                  25                  30

Leu Val Pro Gly Cys His Gly Ser Glu Pro Cys Ile Ile His Arg Gly
        35                  40                  45

Lys Pro Phe Gln Leu Glu Ala Val Phe Glu Ala Asn Gln Asn Ser Lys
    50                  55                  60

Thr Ala Lys Ile Glu Ile Lys Ala Ser Ile Asp Gly Leu Glu Val Asp
65                  70                  75                  80

Val Pro Gly Ile Asp Pro Asn Ala Cys His Tyr Met Lys Cys Pro Leu
                85                  90                  95

Val Lys Gly Gln Gln Tyr Asp Ile Lys Tyr Thr Trp Asn Val Pro Lys
            100                 105                 110

Ile Ala Pro Lys Ser Glu Asn Val Val Val Thr Val Lys Val Met Gly
        115                 120                 125

Asp Asp Gly Val Leu Ala Cys Ala Ile Ala Thr His Ala Lys Ile Arg
    130                 135                 140

Asp
145

<210> SEQ ID NO 4
<211> LENGTH: 129
<212> TYPE: PRT
<213> ORGANISM: Dermatophagoides pteronyssinus

<400> SEQUENCE: 4

Asp Gln Val Asp Val Lys Asp Cys Ala Asn His Glu Ile Lys Lys Val
1               5                   10                  15

Leu Val Pro Gly Cys His Gly Ser Glu Pro Cys Ile Ile His Arg Gly
            20                  25                  30

Ala Pro Phe Gln Leu Glu Ala Val Phe Glu Ala Asn Gln Asn Ser Ala
        35                  40                  45

Thr Ala Lys Ile Glu Ile Lys Ala Ser Ile Asp Gly Leu Glu Val Asp
    50                  55                  60

Val Pro Gly Ile Asp Pro Asn Ala Cys His Tyr Met Lys Cys Pro Leu
65                  70                  75                  80

Val Ala Gly Gln Gln Tyr Asp Ile Lys Tyr Thr Trp Asn Val Pro Ala
                85                  90                  95

Ile Ala Pro Ala Ser Glu Asn Val Val Val Thr Val Lys Val Met Gly
            100                 105                 110

Asp Asp Gly Val Leu Ala Cys Ala Ile Ala Thr His Ala Ala Ile Arg
        115                 120                 125

Asp

VARIANTS OF ALLERGENIC PROTEINS OF THE GROUP 2 OF DERMATOPHAGOIDES

This application claims priority to Italian application MI2000A001986 filed on Sep. 12, 2000.

The present invention relates to novel variants of an allergen of mites of the species *Dermatophagoides pteronyssinus.*

More particularly, the present invention relates to the amino acidic sequences of hypoallergenic variants of the allergen Der p 2, obtained by site-specific mutagenesis of the nucleotidic sequence encoding for said allergen. The hypoallergenic variants can be used in the specific immunotherapy of allergic pathologies caused by dust mites.

BACKGROUND OF THE INVENTION

Allergies are immediate hypersensitivity reactions caused by the production of IgE class antibodies following contact with allergens. IgEs bind to specific receptors located at the surface of effector cells (basophiles and mast cells) and when exposed again to the allergen they induce degranulation of said cells, which release mediators such as histamine and leukotrienes, responsible for the known symptoms of allergies: rhinitis, conjunctivitis, atopic dermatitis and asthma.

*Dermatophagoides pteronyssinus* and *Dermatophagoides farinae* are two similar species of mites present in house dust. The allergens deriving from these arthropods have remarkable importance in clinic.

Nine different types of mites allergens have up to now been identified, the main two being Der p 1 (Der f 1) and Der p 2 (Der f 2), each of them immunoreacting with IgEs in about 80% of allergic subjects.

The allergen Der p 2 (whose nucleotidic sequence is identified in GenBank under the access code AF276239) is a protein consisting of 129 amino acidic residues with a molecular weight of about 14 kD, which contains 3 disulfide bonds essential for its immunogenicity [1, 2]. It has no sequence homology with any other known protein, except Der f 2 (GenBank access code D10449).

The only etiological treatment of allergies is represented by specific hyposensitizing immunotherapy (SIT). This consists in administering increasing doses of the substance which causes the allergy, thus inducing gradual desensitization to said substance in the patient (3).

Immunotherapy however, although constituting an established treatment for allergies, is not completely free from risks (4).

As even serious side effects can occur during such therapy, reasearches have been focused towards the use of non-injective routes (oral/sublingual) for the administration of vaccines and the production of hypoallergenic variants of the proteins used as vaccines, obtained through modification of the allergens by chemical treatments or site-specific mutagenesis [5].

BRIEF DESCRIPTION OF THE DRAWINGS

FIG. 1 demonstrates the results of a western blot analysis of IgE reactivity of a modified Der p 2 allergen.

FIG. 2 demonstrates the results of an Elisa assay showing IgE reactivity of a modified Der p2 allergen.

DETAILED DISCLOSURE

A novel cDNA encoding for the major allergen Der p 2 of *Dermatophagoides pteronyssinus,* whose nucleotide sequence is reported in SEQ ID No. 1, has now been isolated by RT-PCR. It differs from the sequence present in GenBank in 8 positions. The protein coded by the isolated clone, reported in SEQ ID No. 3, differs from the allergen Der p 2 by two residues, Ala16 and Ser63.

It has now been found that the allergenic effect of the mature protein Der p 2, which is produced by removal of residues 1–16 from SEQ ID No. 3, may be reduced by changing its amino acidic sequence in at least one of the positions n. 33, 48, 82, 96, 100, 126, where a lysine residue is present.

"Change" herein means substituting one or more residues at the specified positions, preferably with neutral or polar amino acids, or deleting one or more Lys residues present in the natural form, or simultaneously substituting and deleting two or more residues.

The mutations by substitution, introduce a residue of the amino acid alanine in each of the 6 positions indicated above. Most preferred is the variant in which the six substitutions indicated in SEQ ID No. 4 are present at the same time.

The present invention also comprises the variants of the protein Der p 2, homologous to it by more than 85%, which have at the corresponding positions of their amino acidic sequence the same substitution/deletion pattern as described above for Der p 2, in particular the protein Der f 2.

The invention further comprises an immunologically active peptide deriving from the amino acidic sequence of Der p 2, or from an homologous sequence thereof, and containing at least one of the substitutions/deletions described above.

In a further aspect, the invention is directed to a nucleic acid molecule encoding for a mutation variant of Der p 2, for an homologous variant thereof, or for a peptide derived therefrom, as precised above.

The sequence variants according to the invention can easily be prepared starting from the cDNA of mature Der p 2, or of an homologous variant thereof, in which the region coding the signal peptide is absent and the desired mutations have been introduced.

The cDNA sequence (mutagenized bases in bold print) coding the preferred variant with the 6 substitutions (SEQ ID No. 4), is reported in SEQ ID No. 2.

The produced recombinant protein has reduced IgE reactivity in the serum from subjects allergic to *Dermatophagoides pteronyssinus* mites. In particular, Western blotting assays carried out using a pool of sera from subjects allergic to mites with RAST 4+ reactivity, proved that the IgE reactivity of the variant reported in SEQ ID No. 4 decreases on the average by about 90% compared with that of the normal protein produced in *Escherichia coli* [FIG. 1]. This result was confirmed with ELISA assays, which allowed to identify epitopes in proteins in the native conformation, including conformational epitopes [FIG. 2].

The invention further relates to an expression vector comprising a nucleic acid molecule coding for any one of the hypoallergenic variants defined above.

Said vector can be a plasmid, cosmid, virus, bacteriophage or any other vector commonly used in genetic engineering, and can include, in addition to the nucleic acid molecule of the invention, eukaryotic or prokaryotic elements for the control of the expression, such as regulatory sequences for the initiation and the termination of the transcription, enhancers, promoters, signal sequences and the like.

Moreover, the invention comprises a prokaryotic or eukaryotic host cell transformed into or transfected with the vector of the invention. In principle, prokaryotic cells such as *Escherichia coli* or *Bacillus subtilis*, or eukaryotic cells such as *Saccharomyces cerevisiae* will be used for cloning the vector and expressing the cDNA.

The protein variants of the invention can be produced either as such or as fusion proteins.

Thanks to the reduced IgE reactivity, said variants may be used for therapeutical purposes in the preparation of vaccines to be used in the immunotherapy of allergies due to dust mites.

A further aspect of the invention relates therefore to a pharmaceutical composition comprising an effective amount of the hypoallergenic variant of the invention, optionally in combination with other allergens, natural or modified of mites of the genus Dermatophagoides or of similar genera, together with pharmaceutically acceptable excipients.

In a preferred embodiment, said pharmaceutical composition is a vaccine for use in the prophylactic or therapeutical treatment of allergic diseases, such as bronchial asthma, allergic rhinitis, allergic dermatitis, allergic conjunctivitis. Vaccination principles and practice are well known to those skilled in the art and are described, for example, in (7) and (8).

The following examples illustrate the invention in greater detail.

EXAMPLES

The methods used in the following examples, if not otherwise specified, are those described by Sambrook, Fritsch E T Maniatis "Molecular cloning. A laboratory manual" II Ed vol. 1-2-3 CSH Lab Press 1989.

Example 1

Isolation of cDNA of Der p 2 with RT-PCR mRNA of *Dermatophagoides pteronyssinus* was used to produce the corresponding cDNA by RT-PCR, using a poly-dT oligonucleotide as primer for the reaction catalyzed by the enzyme reverse transcryptase. After that, the cDNA corresponding to the allergen Der p 2 was selectively amplified by PCR (Polymerase Chain Reaction), using two specific primers, each of 15 nucleotides, corresponding to the end of the gene region encoding for the protein. cDNA of Der p 2 was cloned in a vector (pBluescript—Stratagene) for the amplification in *Escherichia coli* cells and sequenced according to the Sanger method with an automated sequencer.

Example 2

Site-specific Mutagenesis of the cDNA Coding for the Allergen Der p 2

The site-specific mutagenesis of the cDNA coding for the allergen Der p 2 is carried out by PCR amplification (Polymerase Chain Reaction) of the same cDNA cloned in a prokaryotic vector (pBluescript). The oligonucleotides used as primer for the PCR reaction have the required substitutions of bases. For each mutagenesis, a complementary pair of said oligonucleotides has been used, which bind to corresponding regions of the two DNA strands. After amplification, the original, unchanged template is selectively degraded by enzymatic digestion catalyzed by the restriction enzyme Dpn 1. *Escherichia coli* cells are then transformed with the mutagenized molecules. Clones obtained from single bacterial colonies are sequenced according to the Sanger method to verify the correct modification of the bases and the absence of cDNA aspecific mutations.

Example 3

Production of the Protein Der p 2 and of the Variant Thereof

Normal cDNA from Der p 2 and mutagenized cDNA, corresponding to SEQ ID No. 2, after cloning in an expression vector (pCALn—Stratagene), are expressed in *Escherichia coil* cells according to standard protocols, wherein the culture in esponential growth (O.D. 600 nm=0.6) is added with of IPTG (isopropyl-β-D-thiogalactopyranoside) for inducing the expression of cDNA. The recombinant proteins are isolated 2 hrs after induction of their synthesis by lysis of the bacterial cells through sonication and removal of cell particulates by centrifugation. Proteins are purified from supernatant by affinity chromatography, using columns wherein the matrix is bonded to the calmodulin protein, which interacts with the CBP portion (Calmodulin Binding Protein) fused to the allergen.

Example 4

Western Blotting Assay of the Allergenicity of the Der p 2 Variant

Equal amounts of the normal recombinant allergen and of the mutagenized variant indicated in SEQ ID No. 4 are analyzed by electrophoresis on polyacrylamide gel and subsequent transfer onto nitro-cellulose membrane by electroblotting, according to the technique described by Towbin (6).

The membrane is incubated for an hour in TBS containing 5% of powder milk (saturation buffer) then overnight with single sera from patients allergic to mites with reactivity RAST 4+. After three washings with TBS containing 0.05% Tween-20, IgE antibodies bonded to the membrane are detected by incubation for an hour with anti-human IgE peroxidase-conjugated antiserum and, after further washings, with the detection system based on the use of a DAB (diaminobenzidine) solution containing $H_2O_2$ as substrate for the peroxidase.

Example 5

ELISA Assay for the Reactivity to IgE of the Der p 2 Variant

Equal amounts (0.1 μg) of normal allergen and of its mutagenized variants, in carbonate/bicarbonate 50 mM buffer, pH 9.6, are adsorbed on wells of polystyrene plates for ELISA tests by incubation at 4° C. for 16 hours. The antigens are then washed with washing solution (60 mM phosphate buffer pH 6.5 containing 0.05% Tween-20) and the free sites are saturated with diluent solution (25% horse serum, EDTA 1 mM, 0.05% Tween 20, 0.01% Thiomersal in phosphate buffer 150 mM pH 7.4). Serial dilutions of human serum pools with RAST 4+ reactivity are prepared in a 1:2 ratio in diluent buffer. Equal amounts (100 μl) of the various serum dilutions are added to each sample and incubated at 25° C. for 2 hours. After three washings, the anti-human IgE peroxidase-conjugated antiserum diluted 1:1500 in diluent buffer is added, and incubated at 25° C. for 1.5 hours. After three washings, the colorimetric reaction is developed by addition of 100 μl of Ultra Blu reagent (Intergen, Milford, Mass.) and incubation for 15 minutes at 25° C. The reaction is stopped by addition of 100 μl of 1N HCl and evaluated at 450 nm with a spectrophotometer.

References

1) Chua K. Y., Doyle C. R., Simpson R. J., Turner K. J., Stewart G. A., Thomas W. R., (1990) "Isolation of cDNA coding for the major mite allergen Der p II by IgE plaque immunoassay".
Int. Arch. Allergy Appl. Immunol. 91 (2): 118–123

2) Smith A. M., Chapman M. D., (1996) "Reduction of IgE binding to allergen variants generated by site-directed mutagenesis: contribution of disulfide bonds to the antigenic structure of the major house dust mite allergen Der p 2".
Mol. Immunol. 33 (4–5): 399–405

3) Theodoropoulos D. S., Lockey R. F., (2000) "Allergen immunotherapy: guidelines, update, and recommendations of the World Health Organization".
Allergy Asthma Proc. 21 (3): 159–166

4) Ohashi Y., Nakai Y., Tanaka A., Kakinoki Y., Washio Y., Ohno Y., Yamada K., Nasako Y., (1998). "Risk factors for adverse systemic reactions occurring during immunotherapy with standardized Dermatophagoides farinae extracts".
Acta Otolaryngol. Suppl. 538: 113–117

5) Ferreira F., Ebner C., Kramer B., Casari G., Briza P., Kungl A. J., Grimm R., Jahn-Schmid B., Breiteneder H., Kraft D., Breitenbach M., Rheinberger H. J., Scheiner O., (1998). "Modulation of IgE reactivity of allergens by site-directed mutagenesis: potential use of hypoallergenic variants for immunotherapy".
FASEB J. 12: 231–242

6) Towbin J., Staehelin T., Gordon J., (1979). "Electrophoretic transfer of proteins from polyacrylamide gels to nitrocellulose sheets: procedures and some applications".
Proc. Natl. Acad. Sci. USA, 76: 4350–4354

7) Paul, (1989), "Fundamental Immunology", Raven press, New York.

8) Cryz, S. J. (1991), "Immunotherapy and Vaccines", VCH Verlagsgesellschaft.

What is claimed is:

1. A variant of a Der p 2 allergen, comprising a mature Der p 2 protein exhibiting at least 85% sequence identity to amino acids 17–145 of SEQ ID No. 3, wherein at least four of the Lys residues present at positions 33, 48, 82, 96, 100, and 126 of Der p 2 are substituted with neutral or polar amino acids, and wherein said variant exhibits reduced IgE reactivity in serum from patients allergic to *Dermatophagoides pteronyssinus* mites as compared to natural Der p 2 allergen.

2. A pharmaceutical composition, comprising:
   a variant of a Der p 2 allergen according to claim 1, together with pharmaceutically acceptable excipients.

3. The variant according to claim 1, wherein said residues are substituted with alanine.

4. A variant of the natural form of Der p 2, comprising SEQ ID No. 4.

5. The variant according to claim 4, consisting of SEQ ID No. 4.

6. A pharmaceutical composition, comprising a variant according to claim 4, together with pharmaceutically acceptable excipients.

* * * * *